(12) United States Patent
Adell

(10) Patent No.: US 9,526,591 B2
(45) Date of Patent: Dec. 27, 2016

(54) PROCEDURE AND DEVICE FOR ENABLING A DENTAL ELEMENT TO BE APPLIED TO A DENTAL ARCH

(75) Inventor: Loren S. Adell, Sunnyvale, TX (US)

(73) Assignees: Loren S. Adell, Sunnyvale, TX (US); Michael Adell, Sunnyvale, TX (US)

( * ) Notice: Subject to any disclaimer, the term of this patent is extended or adjusted under 35 U.S.C. 154(b) by 835 days.

(21) Appl. No.: 13/200,004

(22) Filed: Sep. 14, 2011

(65) Prior Publication Data

US 2013/0065192 A1 Mar. 14, 2013

(51) Int. Cl.
*A61C 7/14* (2006.01)

(52) U.S. Cl.
CPC .................. *A61C 7/146* (2013.01)

(58) Field of Classification Search
CPC ...................................... A61C 7/146
USPC ................ 433/2, 3, 8, 24; 128/859, 861
See application file for complete search history.

(56) References Cited

U.S. PATENT DOCUMENTS

| 4,501,554 A * | 2/1985 | Hickham ................ 433/24 |
| 4,526,540 A * | 7/1985 | Dellinger ............... 433/24 |
| 4,657,508 A * | 4/1987 | Dellinger ............... 433/24 |
| 5,931,667 A * | 8/1999 | Papandreas ............. 433/8 |
| 7,404,714 B2 * | 7/2008 | Cleary et al. .......... 433/24 |
| 2006/0068353 A1 * | 3/2006 | Abolfathi et al. ....... 433/6 |

* cited by examiner

*Primary Examiner* — Edward Moran
(74) *Attorney, Agent, or Firm* — George L. Boller

(57) ABSTRACT

A process of applying at least one dental element to a patient's arch employs a device having a support tray shaped to fit to at least a portion of a patient's dental arch. A formed, liquid-soluble material (such as a thin starch layer formed from a starch sheet) is supported by the support tray and holds at least one dental element in a location for allowing an exposed surface of the at least one dental element to be applied to a patient's dental arch. Afterwards, the support tray is removed from the liquid-soluble material and the liquid-soluble is removed by dissolving it in a liquid, such as water.

1 Claim, 4 Drawing Sheets

PROCEDURE AND DEVICE FOR ENABLING A DENTAL ELEMENT TO BE APPLIED TO A DENTAL ARCH

FIELD OF THE INVENTION

This invention relates to dentistry. In particular the invention relates to a procedure and a device for enabling a dental element to be applied to a dental arch.

BACKGROUND OF THE INVENTION

Various procedures can be used for bonding a dental element, such as an orthodontic bracket, to a tooth of a patient's dental arch. For example, an orthodontic bracket may simply be placed against a desired area of the labial or lingual surface of an individual tooth and bonded to the tooth. Proper location of an orthodontic bracket depends on the skill of the orthodontist. Properly locating and then bonding orthodontic brackets on a tooth-by-tooth basis may not be an efficient use of patient or orthodontist time.

A more efficient procedure involves first creating a model of the entirety or a portion of an individual's dental arch in any of various ways such as by taking an arch impression and then using the arch impression to create the model from any suitable material. Orthodontic brackets are then located at desired locations on and temporarily adhered to individual teeth of the model by a releasable material, such as wax or a weak adhesive. Next a material which is initially shapeable, but will eventually assume a shape for holding the brackets in the positions at which they have been temporarily adhered to the teeth, is applied over each bracket in a manner extending continuously from one bracket to the next. Silicone is an example of such a material. Once the material ceases to be shapeable, it and the brackets which it is holding in their desired positions are removed from the model. After any residual adhesive has been removed from the brackets, the resulting device is ready to be applied to the patient's arch.

When the device is first applied, it can be placed to verify correct position of the brackets. Once that has occurred, the brackets are bonded to the teeth using any suitable process which creates a sufficiently strong bond for the particular orthodontic objective to be achieved. After the brackets have been bonded, the material which has been holding them is removed.

Silicone can be pulled off, but the silicone may separate from portions which lodged in undercuts and/or grooves of orthodontic brackets. Removal of the residual silicone fragments is typically performed manually using a pick.

SUMMARY OF THE INVENTION

Briefly, this disclosure introduces a novel procedure and device for enabling a dental element to be applied to a person's dental arch.

The procedure comprises: creating a model of at least a portion of a patient's dental arch; releasably retaining a dental element, such as an orthodontic bracket, at a desired surface location on the model via an interface which interfaces mutually confronting surfaces of the dental element and the model; placing a sheet, which is both formable and liquid-soluble, in covering relation to a sufficient portion of the dental element and a sufficient portion of the model to enable the sheet to be formed to a shape which dimensionally captures the dental element and holds it in the position it has on the model; forming the sheet to a formed shape which dimensionally captures the dental element and holds it in the position it has on the model; and separably fitting a support tray, which is releasable from the formed sheet, to the model in covering relation to at least a portion of the formed sheet.

The dental element, the formed sheet, and the support tray are removed from the model and applied to a patient's dental arch to place the one of the mutually confronting surfaces belonging to the dental element in confronting relation to a confronted surface of the patient's dental arch, and then bonding the one confronting surface belonging to the dental element to the confronted surface of the patient's dental arch.

Then the support tray is removed from the formed sheet, and the formed sheet is dissolved by applying dissolving liquid to the formed sheet.

A disclosed embodiment of formed sheet comprises material which is water-soluble, enabling the formed sheet to be dissolved by applying water to it.

The device which is used in the procedure which has just been described comprises a support tray shaped to fit to at least a portion of a patient's dental arch, and liquid-soluble material which is supported by the support tray and which captures and holds at least one dental element in a location for enabling an exposed surface of the at least one dental element to be applied to a patient's dental arch.

The foregoing summary, accompanied by further detail of the disclosure, will be presented in the Detailed Description below with reference to the following drawings that are part of this disclosure.

DETAILED DESCRIPTION

Figure 1:
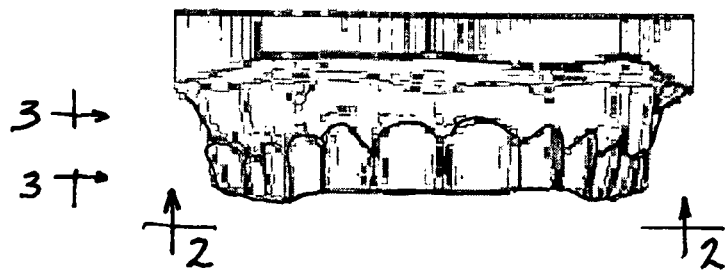
FIG. 1 is an anterior view of a model of a person's upper dental arch.
Figure 2:
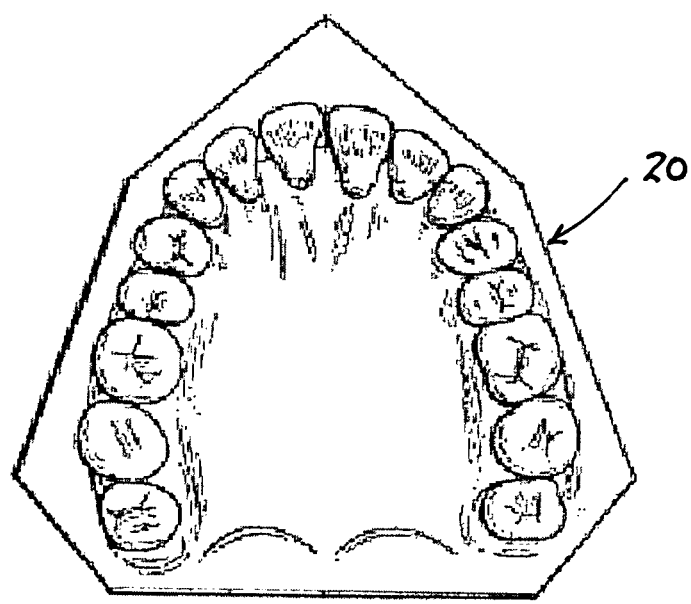
FIG. 2 is a view of the dental arch model in the direction of arrows 2-2 in FIG. 1.
Figure 3:
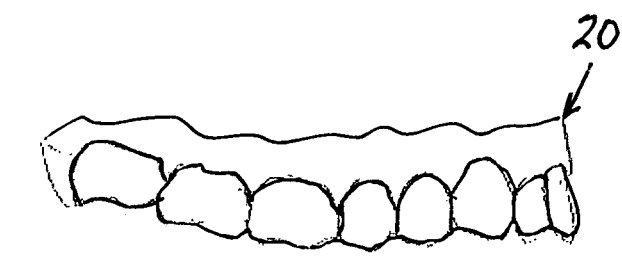
FIG. 3 is in the direction of arrows 3-3 in FIG. 1.

The disclosed procedure comprises creating a model of a patient's entire dental arch or a portion of the arch and then mounting at least one dental element on the model. FIGS. 1, 2, and 3 show a model 20 of a person's entire upper dental arch.

Figure 4:
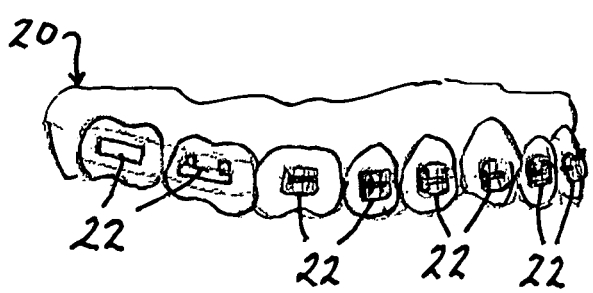
FIG. 4 is a view of FIG. 3 after orthodontic brackets have been placed on teeth of the dental arch model.

FIG. 4 shows orthodontic brackets 22 releasably adhered to individual teeth of model 20.

Figure 5:
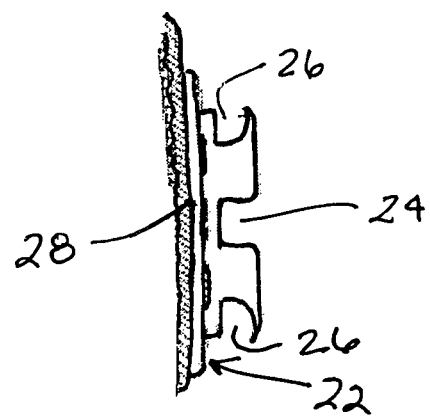
FIG. 5 is an enlarged lateral view of an orthodontic bracket which has been placed on a front tooth of the dental arch model.

As shown in FIG. 5, a representative orthodontic bracket 22 has structure defining an arch wire groove 24 and undercuts 26. Bracket 22 also has a posterior surface 28 which confronts, and via which the bracket is releasably held in place on, a confronted surface of a tooth of model 20.

The disclosed procedure comprises creating model 20 and then mounting orthodontic brackets 22 such that each is releasably held in place at a desired surface location on a tooth of the model. Posterior surface 28 and the confronted surface of the tooth form an interface between the bracket and the model. While the drawings illustrate an example of applying brackets only to labial tooth surfaces, other examples (not illustrated) may involve applying brackets to lingual surfaces only or to both lingual and labial surfaces.

Figure 6:
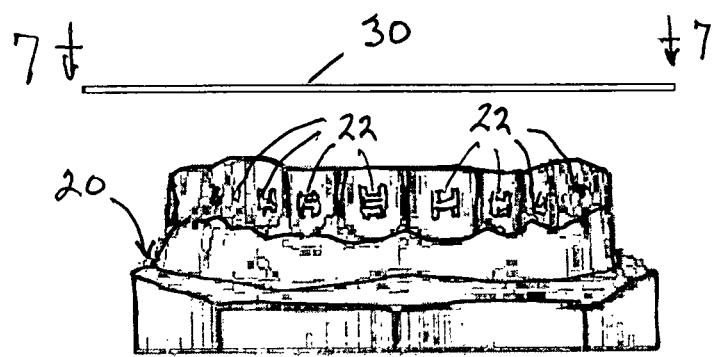
FIG. 6 is a front elevation view illustrating a step of the disclosed procedure.
Figure 7:
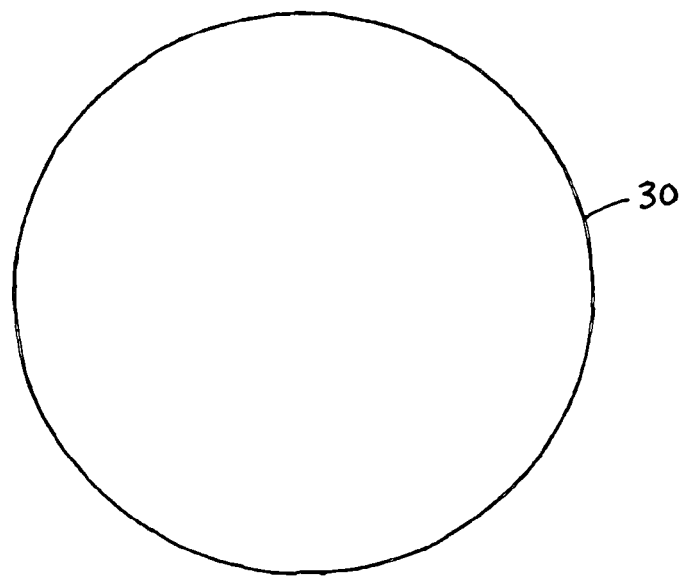
FIG. 7 is a view in the direction of arrows 7-7 in FIG. 6.

Next as shown in FIG. 6, a sheet 30, which is both formable and liquid-soluble, has a shape which, when properly placed over a sufficient portion of each orthodontic bracket 22 and a sufficient portion of the corresponding tooth, enables sheet 30 to be subsequently formed to a shape which will dimensionally capture each bracket 22 and the corresponding tooth and will hold each bracket in the position at which it is being releasably held. The initial size and shape of sheet 30 depend on various factors. Besides the size of the model to which sheet 30 is to be applied, the sheet's size and shape may be a function of a particular machine which is used to form the sheet to its formed shape which captures and holds the brackets on the teeth. FIG. 7 shows an example of sheet 30 having an initial circular shape.

Figure 8:
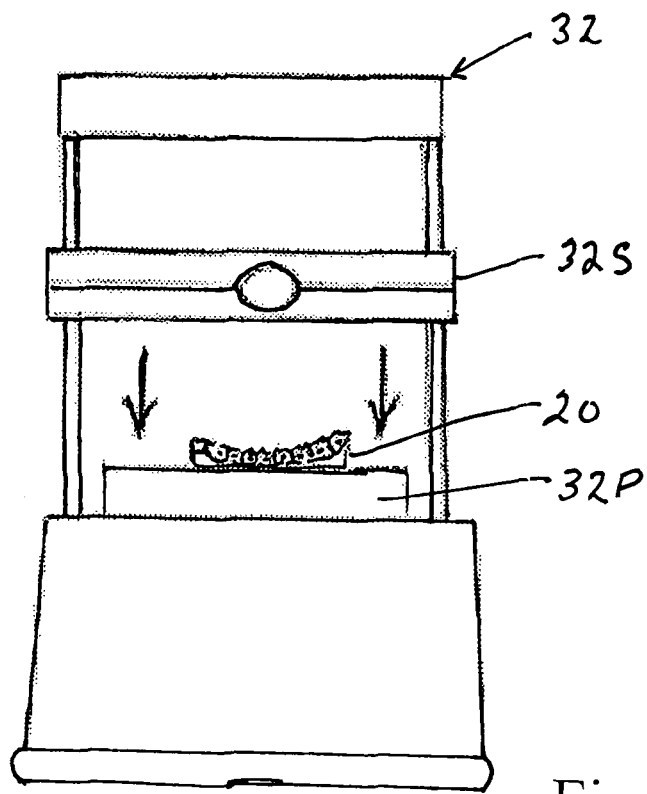
FIG. 8 illustrates a machine which performs the step of FIG. 6.

An example of a machine which can be used to form sheet 30 to formed shape for dimensionally capturing brackets 22 on model 20 and holding them in place is a thermoforming machine 32 shown in FIG. 8. The formed shape is depicted by the shaded area in FIG. 9 which by way of example captures the entirety of each bracket 22.

Figure 9:
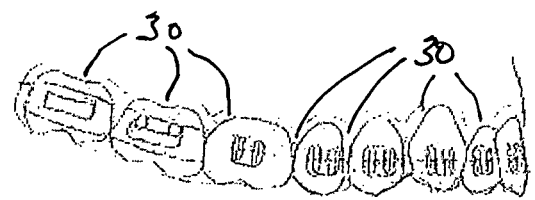
FIG. 9 is a lateral view of the dental arch model after the machine has performed the step of FIG. 6.

Thermoforming machine 32 comprises a platen 32P on which model 20 is placed with the teeth pointed upward. A slide 32S overlies platen 32P and functions to hold a circular sheet 30 which has not yet been formed. Slide 32S moves downward to place sheet 30 over model 20, and after placement, to heat sheet 30 just enough to cause it to form around the teeth of model 20 and orthodontic brackets 22, thereby capturing the brackets and holding them in place on the teeth. Some of the material of sheet 30 may form in undercuts 26 and/or arch wire groove 24. While the size of sheet 30 is large enough to capture and hold all brackets, excess material around the perimeter of the formed sheet may be cut away to leave the formed shape as shown in FIG. 9.

Figure 10:
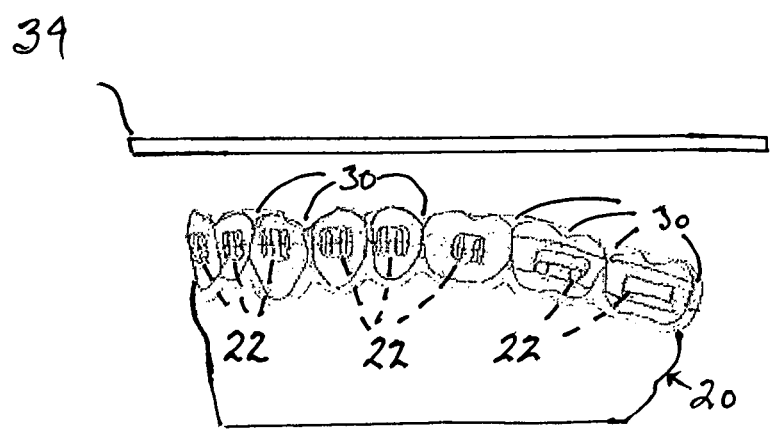
FIG. 10 is a lateral elevation view illustrating a further step of the disclosed procedure.
Figure 11:
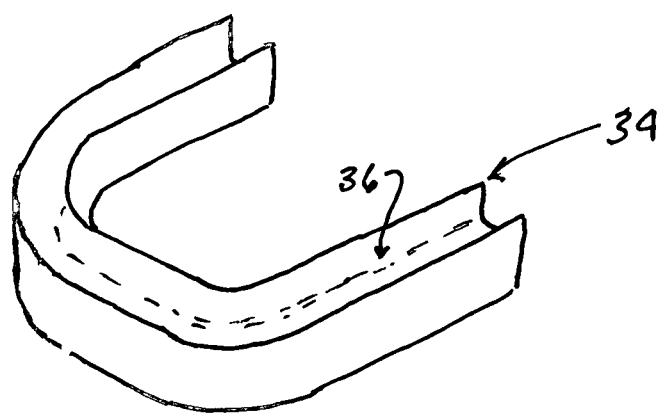
FIG. 11 is a perspective view illustrating by itself a support tray created by the step of FIG. 10.

Next, a support tray 34, shown by itself in FIG. 11, is created by a step shown in FIG. 10. A sheet of material 34 from which the support tray is formed is placed in slide 32S and the slide is moved to place sheet 34 over and against formed sheet 30. Slide 32S heats the sheet to form the support tray in situ on model 20 in covering relation to at least a portion of formed sheet 30. Support tray 34 has a nominal thickness greater than that of sheet 30 and supports formed sheet 30 by its channel 36 fitting closely to the sheet but without intruding into arch wire groove 24 and undercuts 26 in a way which would interfere with or prevent the tray from being separated from formed sheet 30 after brackets 22 have been bonded to teeth of a patient's arch. Support tray 34 does have some flexibility which enables it to be separated from formed sheet 30 after brackets 22 have been bonded to teeth of a patient's arch. Depending on the location of a bracket on a tooth, support tray 34 may be formed to completely cover the portion of formed sheet 30 holding a bracket, to partially cover the portion of formed sheet 30 holding a bracket, or to leave the portion of formed sheet 30 holding a bracket uncovered.

After the step of FIG. 10, support tray 34 and formed sheet 30 are removed from model 20. Because orthodontic brackets 22 are held captured in position by formed sheet 30, they separate from model 20 with sheet 30 and support tray 34.

Support tray 34 is then used to fit brackets 22 to a patient's dental arch by placing surface 28 of each bracket 22 against a confronted surface of the patient's dental arch, after which each bracket is bonded to a tooth of the arch.

Support tray 34 is then removed from formed sheet 30, and the formed sheet is dissolved by applying dissolving liquid to it. The material of formed sheet 30 comprises a starch which can be dissolved in water. A 3.0 mil (0.003 inch) thickness for a starch sheet 30 is suitable and somewhat thicker sheets up to about 5.0 mil may perform satisfactorily. Various materials are suitable for support tray 34. They include polyvinyl chloride (PVC) and similar synthetics. While their thicknesses are typically greater than that of sheet 30 (30 mils is an example of a suitable thickness for PVC), they should be just thick enough to provide proper support and release from formed sheet 30.

While thermoforming is a suitable forming process, other forming processes, such as pressure forming and vacuum forming, are potentially suitable, and various individual processes may be used in combination.

While the specific example shown in the drawings involves applying orthodontic brackets to teeth of a dental arch preparatory to bonding them to the teeth, the disclosed process and device are generic to the application of any of various dental devices to a dental arch which requires locating a device on a person's arch in correspondence with a position at which the device has been placed on a model of the person's arch preparatory to securing the device to the person's arch. An example of a dental device which can be placed other than on a tooth by using the disclosed process is a post for a replacement tooth which is placed in a person's gum tissue.

What is claimed is:

1. A device for use in a process of applying at least one dental element to a patient's arch, the device comprising:

a support tray shaped to fit to at least a portion of a patient's dental arch;

at least one dental element;

and a water-soluble starch which is supported by the support tray and which holds the at least one dental element in a location for enabling an exposed surface of the at least one dental element to be applied to a patient's dental arch;

in which the water-soluble starch has a nominal thickness less than 5.0 mils.

* * * * *